US00PP22104P2

(12) United States Plant Patent
Egger

(10) Patent No.: US PP22,104 P2
(45) Date of Patent: Aug. 30, 2011

(54) ***X HEUCHERELLA* PLANT NAMED 'GOLDEN ZEBRA'**

(50) Latin Name: *X Heucherella*
Varietal Denomination: Golden Zebra

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/800,257

(22) Filed: May 11, 2010

(51) Int. Cl.
*A01H 5/00* (2006.01)

(52) U.S. Cl. ..... Plt./441

(58) Field of Classification Search ..... Plt./441
See application file for complete search history.

*Primary Examiner* — June Hwu
(74) *Attorney, Agent, or Firm* — Klarquist Sparkman, LLP

(57) ABSTRACT

A new and distinct *Heucherella* plant substantially as shown and described, characterized by yellow spring leaves with a strong red pattern along veins, summer leaves yellow green to lime with red to dark brown in over half the leaf center, distinctively lobed, palmately divided leaves, and a medium plant size.

1 Drawing Sheet

Botanical denomination: *X Heucherella.*

Variety designation: 'Golden Zebra'.

The present invention relates to a new and distinct cultivar of *Heucherella* and given the cultivar name of 'Golden Zebra'. *Heucherella* is in the family Saxifragaceae. *Heucherella* 'Golden Zebra' originated from a controlled cross between *Heuchera* 791-5 (a proprietary unreleased *Heuchera villosa* hybrid), as the seed parent, and massed selected *Tiarella* (10), as the pollen parent.

Compared to the seed parent, *Heuchera* 791-5 (unpatented), the new variety has leaves that are deeply cut and yellow with a dark blotch along the vein compared to an uncut rose purple to olive leaf with no blotch.

Compared to the pollen parent, one of a *Tiarella*-10 massed, the new variety has yellow foliage in spring and summer rather than green.

Compared to *Heucherella* 'Stoplight' (U.S. Plant Pat. No. 16,835), this new cultivar has foliage that is deeply cut rather than shallowly lobed.

Compared to *Heucherella* 'Alabama Sunrise' (U.S. Plant Pat. No. 19,611), the new cultivar is smaller and has leaves that are smaller, more yellow, more cut, and has a larger and darker central pattern.

This new *Heucherella* is distinguished by:

1. yellow spring leaves with a strong red pattern along veins,
2. summer leaves yellow green to lime with red to dark brown in over half the leaf center,
3. distinctively lobed, palmately divided leaves,
4. and a medium plant size.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
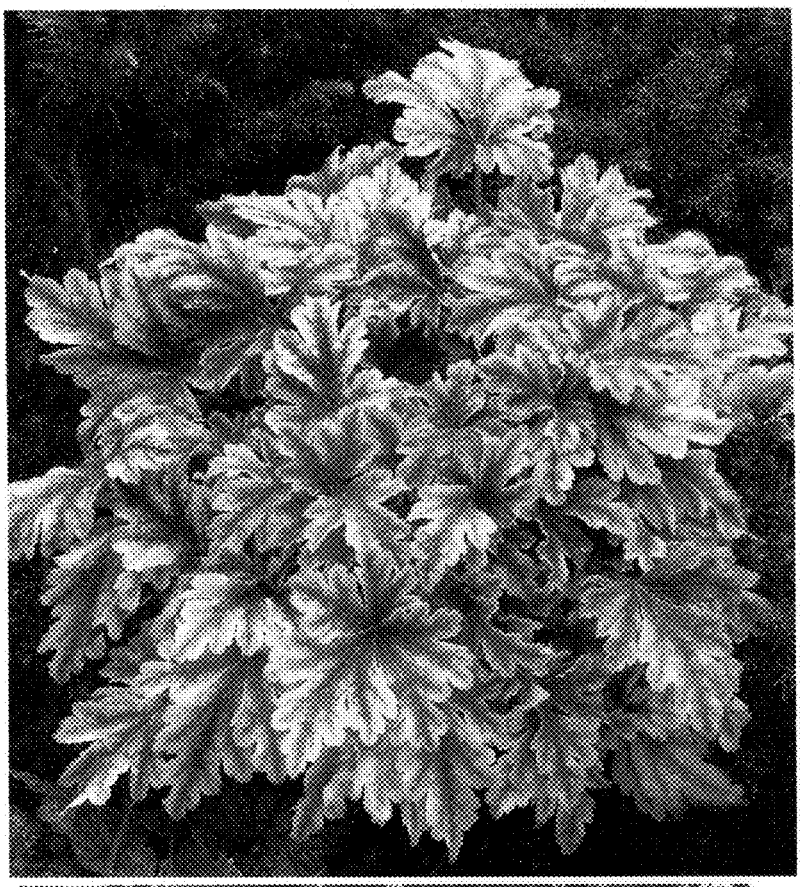
FIG. 1 shows a one year old *Heucherella* 'Golden Zebra' growing in the ground in late spring in shade in Canby, Oreg.
Figure 2:
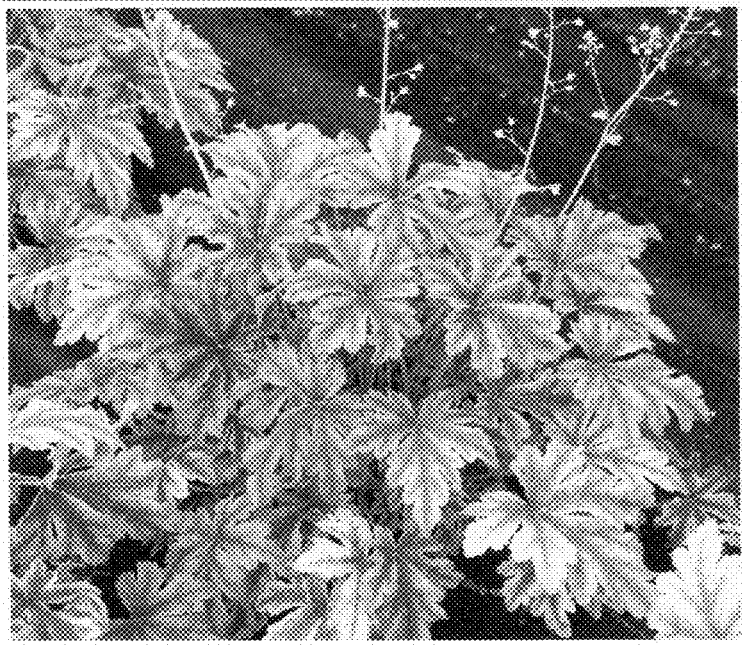
FIG. 2 shows a one year old *Heucherella* 'Golden Zebra' in bloom, planted in the ground in a trial bed in the shade in the summer in Canby, Oreg.

The following is a detailed description of the new *Heucherella* cultivar based on observations of a two-year-old specimens growing in the ground in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, fifth edition.

Plant:

*Form.*—Basal rosette, herbaceous perennial.

*Hardiness.*—USDA Zone 4 to 9.

*Size.*—18 cm tall from top of the foliage to the ground and 43 cm wide.

*Habit.*—Mounding.

*Vigor.*—Excellent.

*Roots.*—Fibrous, freely branching, fine, and white in color. Roots develop easily from cuttings.

Leaf:

*Type.*—Simple.

*Arrangement.*—Rosette.

*Shape.*—Broadly ovate.

*Lobing/division.*—5 lobes palmately parted with the terminal the longest and most deeply parted, each with distinctly cut secondary lobes (the depth of the lobes varies with plant maturity and leaf age; leaves become more deeply lobed with maturity).

*Venation.*—Palmate.

*Margins.*—Crenate.

*Apex.*—Mucronulate.

*Base.*—Cordate, sometimes overlapping.

*Blade size.*—Grows to 11 cm long and 10 cm wide.

*Surface texture.*—Glandular both surfaces.

*Petiole description.*—Grows to 16 cm long and 2.5 mm wide, glandular hairs, between Greyed Orange 177B and Greyed Purple 186B on the bottom and a color closest to Yellow Green 151A, but lighter.

*Leaf color.*—Spring, topside, Yellow Green 151A with the pattern Greyed Red 178A, bottom side, between Greyed Yellow 160A and Yellow Green 151A with the pattern Greyed Orange 177A; summer topside Yellow Green N144C with the pattern Greyed Orange 177A, bottom side Yellow Green N144D with the pattern Greyed Orange 177B; fall/winter topside, some leaves darken with rose and burgundy tones, Greyed Purple 185C to 185A with the pattern Greyed Orange 177A.

Inflorescence:

*Size.*—Grows to 3 cm wide and 33 cm long.

*Type.*—Raceme.

*Number of flowers per raceme.*—About 90.

*Number of raceme.*—10.

*Peduncle.*—10 cm tall, 3 mm wide at base, Yellow Green 146C, glandular hairs.

*Pedicel.*—Variable, with glandular hairs, Greyed Red 182B.

*Bloom period.*—May with sporadic rebloom in Canby, Oreg.

Flower bud:

*Size.*—2.5 mm wide and 3 mm long.

*Description.*—Glandular puberulent, ovoid.

*Color.*—White N155B.

Flower:

*Type.*—Perfect.

*Shape.*—Campanulate.

*Size.*—6 mm deep and 10 mm wide.

*Petal description.*—5 in number, lanceolate, 5 mm long and 0.5 mm wide, tip acuminate, base attenuate, margin entire, glabrous on both sides, White NN155D on both sides.

*Calyx description.*—3 mm deep and 5 mm wide, with 5 lobes, divided ½ way to the base, campanulate, glandular hairs on outside, glabrous inside, tip obtuse, margin entire, NN155D on both sides.

*Stamen description.*—10 in number, filaments 5 mm long, White NN155D, anthers sterile, less than 1 mm, Greyed Orange N167A.

*Pistil description.*—One central two beaked pistil, 6 mm long, White NN155D.

*Fragrance.*—None.

*Lastingness.*—Each raceme blooms for about 2 weeks on the plant.

Fruit and seed: None.

Disease and pest tolerance: No known resistances. All *Heucherella* are susceptible to root weevils.

I claim:

1. A new and distinct *Heucherella* plant as herein illustrated and described.

* * * * *